(12) United States Patent
Catelli

(10) Patent No.: US 6,997,317 B2
(45) Date of Patent: Feb. 14, 2006

(54) DEVICE FOR TAKING BLOOD SAMPLES TO TESTED, FOR EXAMPLE FOR THE LEVEL OF GLUCOSE CONTAINED THEREIN

(75) Inventor: Pietro Catelli, Como (IT)

(73) Assignee: Artsana S.p.A., Grandate (IT)

( * ) Notice: Subject to any disclaimer, the term of this patent is extended or adjusted under 35 U.S.C. 154(b) by 283 days.

(21) Appl. No.: 10/449,032

(22) Filed: Jun. 2, 2003

(65) Prior Publication Data

US 2004/0019250 A1 Jan. 29, 2004

(30) Foreign Application Priority Data

Jun. 26, 2002 (IT) .......................... MI20020334 U

(51) Int. Cl.
*A61B 17/06* (2006.01)
(52) U.S. Cl. ....................................... 206/438; 206/569
(58) Field of Classification Search ................ 206/438, 206/569, 570, 751, 572, 440, 441, 63.3, 63.5; 229/120.03, 120.08, 121, 122, 120.14, 120.15, 229/122.21, 123.2; 220/524
See application file for complete search history.

(56) References Cited

U.S. PATENT DOCUMENTS

| | | | | |
|---|---|---|---|---|
| 1,791,094 A | * | 2/1931 | Albert | ................... 229/120.03 |
| 3,292,839 A | * | 12/1966 | Pike | ............................ 229/215 |
| 4,407,442 A | * | 10/1983 | Watson et al. | .......... 229/120.18 |
| 4,979,515 A | | 12/1990 | Briggs et al. | |
| 4,994,068 A | | 2/1991 | Hufnagle | |
| 5,074,462 A | * | 12/1991 | Countee, Jr. | ................. 229/155 |
| 5,871,145 A | * | 2/1999 | Hermann et al. | ....... 229/120.21 |
| 6,036,924 A | | 3/2000 | Simons et al. | |
| 6,189,778 B1 | * | 2/2001 | Kanter | ..................... 229/122.1 |
| 6,206,192 B1 | * | 3/2001 | Winstead et al. | ............ 206/572 |
| 6,264,619 B1 | * | 7/2001 | Ferguson | ..................... 600/573 |
| 6,347,704 B1 | * | 2/2002 | Dixon | ...................... 206/459.5 |

FOREIGN PATENT DOCUMENTS

| | | |
|---|---|---|
| AU | 3086889 | 9/1989 |
| JP | 2002 102252 | 4/2002 |
| WO | WO 86/00513 | 1/1986 |

* cited by examiner

*Primary Examiner*—Shian T. Luong
(74) *Attorney, Agent, or Firm*—Young & Thompson

(57) ABSTRACT

A device for taking a blood sample to be tested, for example for the level of glucose contained therein, presents a container (1) containing at least one lancet (5) for puncturing a part of the patient's body in order to cause blood to emerge, and at least one tamping element (4) to enable that point of the body from which the blood has emerged to be covered after the blood has been withdrawn, and to facilitate the coagulation and absorption of the residual blood at that point.

11 Claims, 2 Drawing Sheets

DEVICE FOR TAKING BLOOD SAMPLES TO TESTED, FOR EXAMPLE FOR THE LEVEL OF GLUCOSE CONTAINED THEREIN

The present invention relates to a device for taking blood samples.

To take a blood sampling droplet, for example to test the glucose content thereof, it is known to perforate the fingertip of a finger with a finger needle or lancet. The emerging blood is deposited on a suitable support associated with an analyzer element which in known manner carries out the required test, for example for glucose present in the blood. In the meantime, the user or patient who has undergone the blood test has to tamp the finger tip with cotton wool, gauze or another tamping element. The patient therefore has to prepare this gauze or other tamping element before the finger is punctured in order to be ready to tamp the discharge of blood after its sampling and during the test.

Although gauzes and finger lancets have been known and used for some time, no product or device is available commercially which enables in particular a "careless" user to always have available a gauze or similar tamping element each time he is required to undergo a blood test. Such a user frequently does not have (sterile) gauze available after the blood test and tends to tamp the wound with unsuitable and unsterilized products, with obvious drawbacks.

An object of the present invention is to provide a device which solves this problem by enabling a user taking a blood sample to always have a sterile tamping product available and ready for use.

Another object is to provide a simple device of easy use.

These and further objects which will be apparent to the expert of the art are attained by a device in accordance with the accompanying claims.

The present invention will be more apparent from the accompanying drawing, which is provided by way of non-limiting example and in which.

Figure 1:
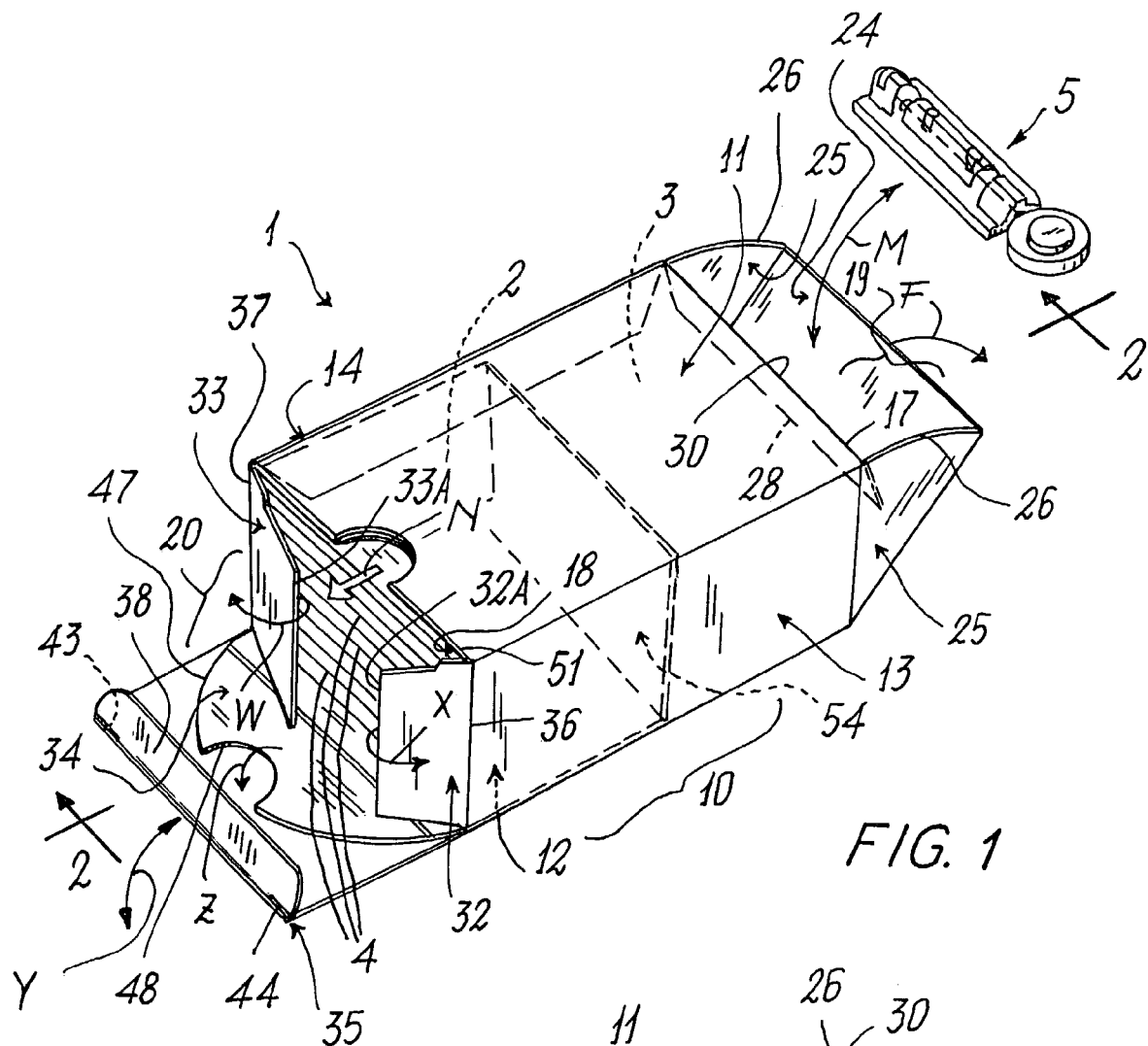
FIG. 1 is a perspective view of a device according to the invention.

With reference to the said figures, a device according to the invention comprises a container 1 in which two separate cavities or chambers 2 and 3 are present, in which, in the example, there are placed a plurality of sterile gauzes and/or pads 4 (inserted in suitable known envelopes) and a corresponding plurality of finger lancets 5, of known type and enabling a patient's blood to be taken for sampling, for example to evaluate the level of glucose present therein. Alternatively, the container 1 can be formed in such a manner that the cavities or chambers 2 and 3 each contain respectively a single gauze 4 or other similar material (such as non-woven fabric) and a single finger lancet.

In the example the container 1 comprises a one-piece body 10 defined by a single punched sheet 10A (for example of papery material such as cardboard or the like) presenting a plurality of parts which when suitably folded define the body 10. This latter is of box type and comprises, with reference to the figures, an upper face 11, a lower face 12, a front face 13, a rear face 14, a right lateral face 15 and a left lateral face 16. In correspondence with the lateral faces 15 and 16 there are provided apertures 17 and 18 closable respectively by corresponding lids 19 and 20. As stated, these latter form part of the single punched sheet 10A defining the body 10 and can be folded or moved away from the respective apertures 17 and 18 to enable at least one lancet 5 (arrow M of FIG. 1) and at least one gauze 4 (arrow N of FIG. 1) to be removed from the body 10.

More specifically, the lid 19 comprises an element movable about a lower end edge 23 of the face 15 (arrow F of FIG. 1) and presenting a wall 24 and sidepieces 25 projecting perpendicular to the wall 24, said sidepieces having a curved free edge 26. The sidepieces 25 become positioned parallel to the faces 13 and 14 of the body within the cavity 3 when the lid 19 intercepts the aperture 17 with its wall 24. When the lid does not intercept said aperture 17, the wall 24 lies inclined to the plane in which the lower face 12 of the body 10 lies, enabling the lancet 5 to be withdrawn.

It should be noted that in the example shown in the figures, the lid 19 is of such a shape as to intercept an aperture 17 which involves substantially the entire lateral face 15 of the body 10, even though said aperture is also partly intercepted by a flap 28 which extends from the upper end edge 30 of the face 11 and acts as a partial restriction for the aperture 17 to enable a single lancet 5 to emerge. Alternatively the lid 19 can intercept an aperture involving only a portion of the lateral face 15, for example that close to the lower edge 23 of said face, In this case, the flap 28 would be prolonged towards said edge, extending from the upper edge 30 of said face 15 by much more than that shown in the example of the figures, said flap being able to be fixed and defining part of the face 15.

In the example shown in the figures the lid 20 is instead defined by a plurality of movable flaps 32, 33, 34 and 35: the flaps 32 and 33 extend from end lateral edges 36 and 37, respectively, of those faces 13 and 14 of the body 10 close to the lateral face 16; these flaps are hinged to said edges 36 and 37 and can rotate about them (arrows W and X of FIG. 1). They are tapered at their free ends 32A and 33A.

The flap 35 is the most outer flap of the aforesaid and completely closes the aperture 20 when a folded portion 38 thereof is brought into contact with the upper face 11 of the body 10 by being inserted into the cavity or chamber 2 to enable the flap 35 to be maintained in its closed position in which it intercepts the aperture 20. The portion 38 presents lateral slots 43 and 44 to cooperate with the flaps 32 and 33 to maintain the flap 35 in its closed position on the aperture 20. The flap 35 moves in accordance with the double arrow Y of FIG. 1 and is hinged to a lateral edge of the lower face 12.

The flap 34 is internal to the flaps 32 and 33, it being positioned between these latter and the cavity 2 of the body 1. It acts as the first element for maintaining the gauzes 4 within the cavity or chamber 2. Although the described embodiment presents various flaps 32, 33, 34 and 35, the expert of the art could form the device 1 with a container even having only a single closure flap, preferably that indicated by 35.

The inner flap 34 moves in accordance with the arrow Z of FIG. 1, and presents in the example a rounded or arcuate edge 47 in which a semicircular recess 48 is provided. The flap 34 is the end part of a portion 50 of the punched sheet 10A which defines the body 10, it being folded several times to also define the upper face 11 of the body 10. This punched sheet portion 50 is folded about an edge 51 of the face 11 defining the upper part of the aperture 18 where a circular aperture 51A is present which when the portion 50 has been folded defines a semicircular recess which facilitates the gripping of the gauzes or pads 4; the semicircular recess derives from the circular aperture 51A by folding the portion 50 along that diameter thereof coinciding with the edge 51 of the face 11.

Figure 2:
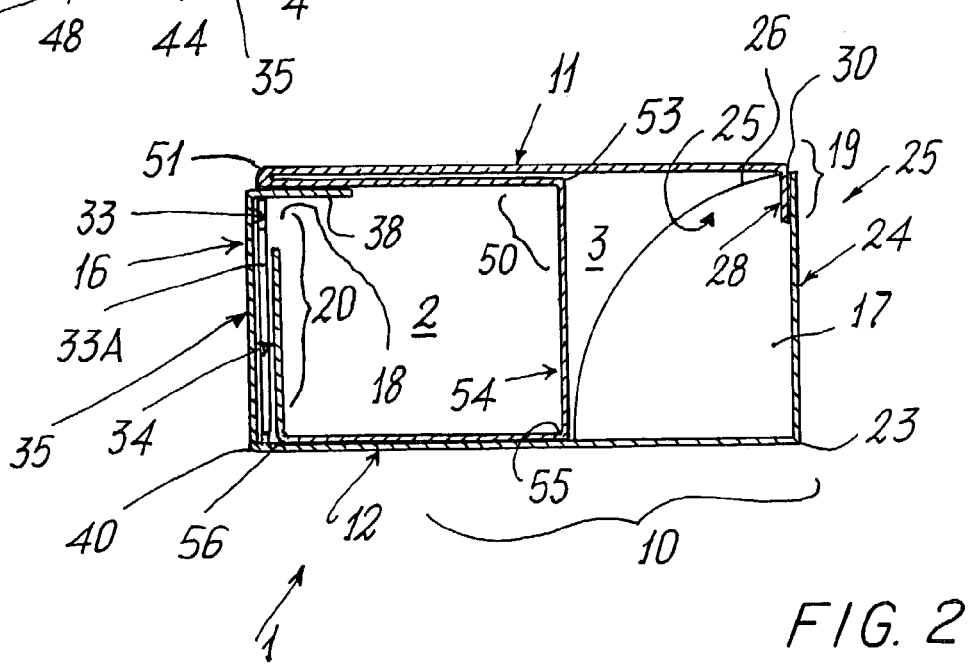
FIG. 2 is a section on the line 2—2 of FIG. 1, but without showing the articles contained in the device of FIG. 1.
Figure 3:
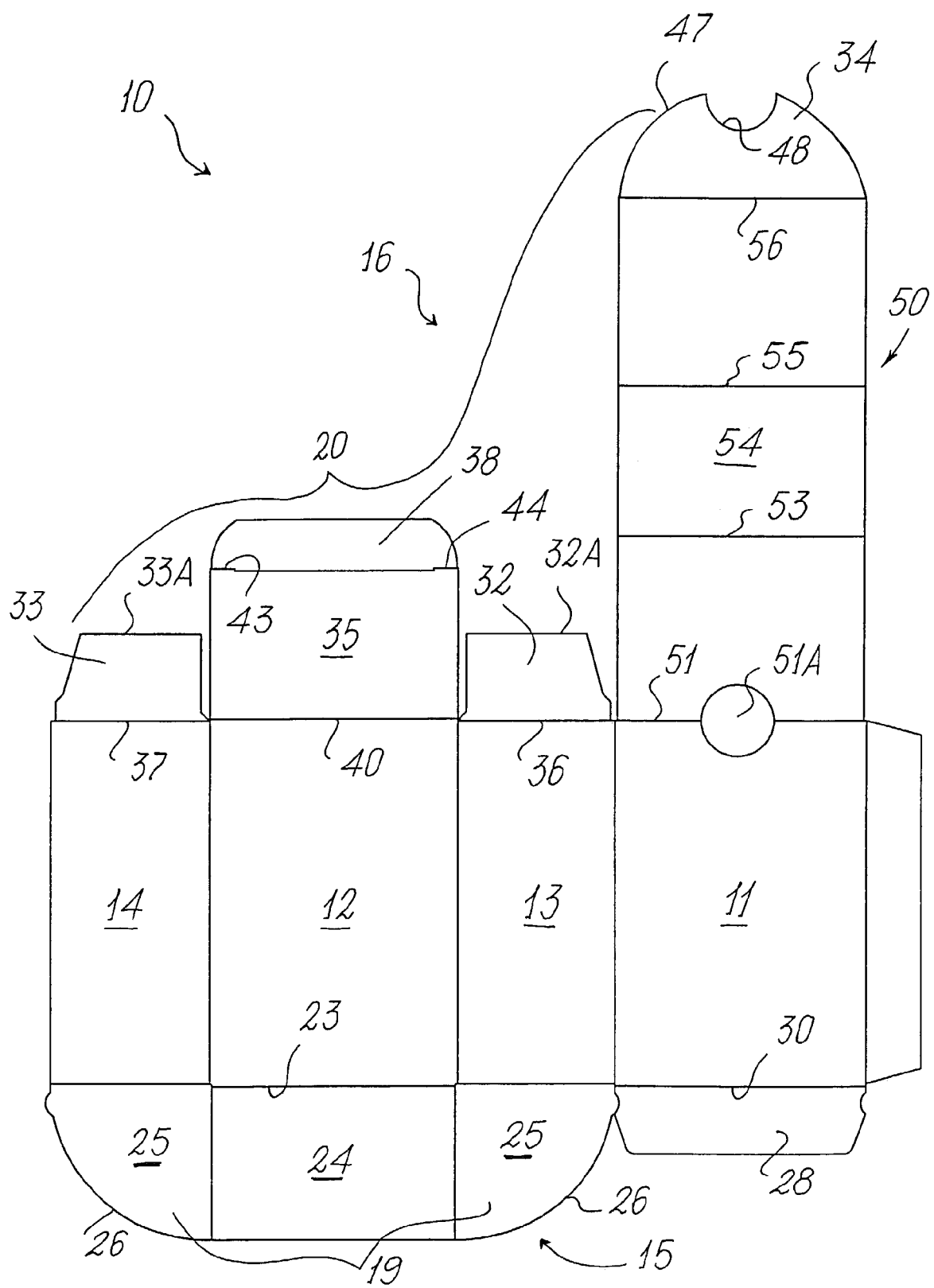
FIG. 3 is a plan view of a punched sheet used to obtain the device of FIG. 1, those parts of the punched sheet identical to those of the device of FIG. 1 being indicated by the same reference numerals.

The punched sheet portion 50 is further folded about an edge 53 (upper in FIGS. 1 and 2) of a dividing wall 54 interposed between the cavities or chambers so as to define this wall. It is then further folded towards the aperture 20 to define the lower edge 55 of the wall 54 and in correspondence with an end edge 56 of the inner flap 34. The folds in the portion 50 are obtained by being made in correspondence with predetermined weakening lines provided in the punched sheet portion 50, said lines defining the edges 51, 53, 55, 56.

By virtue of the invention, a device is provided which contains within it both the finger lancet (or another element for causing blood to discharge from a part of the user's body, generally the tip of a patient's finger) and a gauze or pad to adequately safely, from the medical viewpoint, tamp said discharge of blood; this is done in such a manner as to enable the user taking a sample of his own blood (or carrying out a test to evaluate the presence of a particular characteristic therein) to have available all the useful instruments to conclude his blood test in a safe, clean and rapid manner.

A specific embodiment of the invention has been described. However in the light of the aforegoing description, the expert of the art is able to conceive a device which has the characteristics defined in the following claims but differs in certain details from those already described. For example the container 1 can be wholly or at least partly of plastic construction; the container 1 can be rigid or at least partly rigid and can contain a single gauze and a single lancet (in which case the pack for once-only use can present the gauze secured to the lancet) or a plurality of gauzes and lancets kept separate.

What is claimed is:

1. A device for taking a blood sample to be tested and for tamping the discharge of blood from a part of a patient's body which has been punctured, said puncture being made by a puncturing member (5), the tamping being effected by a tamping element (4), the device comprising a container (1) presenting at least one puncturing member (5) and a least one tamping element (4), said device enabling the patient to take the sample while having immediately available the tamping element (4) to immediately interrupt blood discharge in a manner safe from the medical viewpoint, the container (1) having separate chambers (2, 3) for containing respectively the puncturing member (5) and the tamping member (4), the container (1) comprising a body (10) in which the separate chambers (2, 3) are provided, said body being in one piece, the chambers (2, 3) being separated by a wall (54) formed by folding a punched sheet portion (50) which also defines a face (11) of the body (10) of the container (1).

2. A device as claimed in claim 1, wherein a first chamber (2) contains a plurality of tamping elements (4) and a second chamber (3) contains a plurality of puncturing members (5).

3. A device as claimed in claim 2, wherein the number of tamping elements (4) is equal to the number of puncturing members (5).

4. A device as claimed in claim 1, wherein the body (10) of the container (1) is in one piece and is obtained from a single punched sheet (10A) presenting a plurality of folded parts, said body presenting, in its opposing lateral sides (15, 16), apertures (19, 20) which communicate with the respective separate chambers (2, 3), each tamping element (4) and each puncturing element (5) being removable through said apertures, a corresponding closure element (19, 20) being positioned in correspondence with each aperture.

5. A device as claimed in claim 4, wherein the chamber (3) containing at least one said puncturing element (5) has its aperture (17) occupying at least a part of the corresponding lateral side (15) of the body (10) of the container (1), the closure element (19) positioned in correspondence with said aperture (17) being hinged to an end edge of said lateral side (15) and comprising a part (24) from the edges of which there project sidepieces (25) slidingly inserted into said chamber (3), said part (24) of the closure element (19) lying inclined to the plane of said lateral side (15) when said closure element (19) is in the position in which it frees access to said chamber (3).

6. A device as claimed in claim 4, characterised in that wherein the closure element (20) for the aperture (18) of the chamber (2) containing at least one said tamping element (4) comprises at least one flap (35) hinged to an end edge of that face (12) of the body (10) of the container (1) which on one side bounds said aperture (18).

7. A device as claimed in claim 6, wherein the closure element (20) for the aperture (18) of the chamber (2) for the tamping element (14) comprises a plurality of movable flaps (32, 33, 34, 35).

8. A device as claimed in claim 4, wherein the body (10) of the container (1) is of box shape.

9. A device as claimed in claim 1, wherein the punched sheet portion (50) defining the wall (54) between the separate chambers (2, 3) terminates on the outside of one (2) of these latter and defines a movable flap for closing the aperture (18) of said chamber (3).

10. A device as claimed in claim 1, wherein the container (1) is rigid at least in part.

11. A device as claimed in claim 1, characterised in that the container (1) is flexible at least in part.

* * * * *